United States Patent [19]

Tokuhiro et al.

[11] Patent Number: 5,071,621

[45] Date of Patent: Dec. 10, 1991

[54] METHOD OF SUPPLYING SCENTS TO A ROOM OF A MOTOR VEHICLE

[75] Inventors: Tomoya Tokuhiro; Norihiro Yamaguchi; Hiroaki Watanabe, all of Tokyo, Japan

[73] Assignee: Shimizu Construction Co. Ltd., Tokyo, Japan

[21] Appl. No.: 299,114

[22] Filed: Jan. 19, 1989

[30] Foreign Application Priority Data

Jan. 20, 1988 [JP] Japan ................................ 63-10265

[51] Int. Cl.$^5$ .............................................. A61L 9/00
[52] U.S. Cl. ............................................ 422/4; 422/1; 422/5; 422/120; 422/123; 239/6; 261/DIG. 65; 390/438; 390/464
[58] Field of Search .................... 422/1, 4, 5, 120, 122, 422/123, 124; 239/6, 60; 261/DIG. 65; 340/438, 464

[56] References Cited

U.S. PATENT DOCUMENTS

| | | | |
|---|---|---|---|
| 422,202 | 2/1890 | Furney | 55/216 |
| 1,508,399 | 9/1924 | Kohut | 55/249 |
| 1,758,552 | 5/1930 | Allen | 239/305 |
| 2,555,047 | 5/1951 | Loque | 239/58 |
| 2,614,820 | 10/1952 | Boydjieff | 261/26 |
| 2,686,944 | 7/1950 | Gubelin | 422/124 |
| 3,298,674 | 1/1967 | Gilbertson | 261/30 |
| 3,298,674 | 1/1967 | Gilbertson | 261/30 |
| 3,392,916 | 7/1968 | Engstrom | 239/102.2 |
| 3,490,436 | 1/1970 | Hart | 126/113 |
| 3,531,150 | 9/1970 | Jahnke | 296/1.1 |
| 3,711,023 | 1/1973 | Smith | 239/54 |
| 3,744,722 | 7/1973 | Burns | 239/338 |
| 3,924,810 | 12/1975 | Otterstetter | 239/305 |
| 4,081,139 | 3/1978 | Migliozzi | 239/305 |
| 4,087,495 | 5/1978 | Umehara | 261/81 |
| 4,109,863 | 8/1978 | Olson | 239/102.2 |
| 4,116,387 | 9/1978 | Kremer | 239/338 |
| 4,303,617 | 12/1981 | Bryson | 422/123 |
| 4,595,434 | 9/1987 | Spector | 422/116 |
| 4,601,888 | 6/1986 | Hudgins | 422/116 |
| 4,603,030 | 7/1986 | McCarthy | 422/4 |
| 4,629,604 | 12/1986 | Spector | 422/124 |
| 4,695,434 | 9/1987 | Spector | 422/116 |

FOREIGN PATENT DOCUMENTS 535375 11/1980 Australia .

(List continued on next page.)

OTHER PUBLICATIONS

U.S. Patent Application Ser. No. 07/204,373, filed on Jun. 9, 1988.
U. S. Patent Application Ser. No. 07/358,936, filed on May 26, 1989.
American Heritage Dictionary, Copyright 1982, p. 1266.
U. S. Patent Application Ser. No. 07/476,589, filed on Feb. 6, 1990.
U. S. Patent Application Ser. No. 07/524,801, filed on May 18, 1990.

Primary Examiner—Robert J. Warden
Assistant Examiner—Laura E. Collins
Attorney, Agent, or Firm—Cushman, Darby & Cushman

[57] ABSTRACT

A method of supplying scents to a room of a motor-car. In this method, a scent holder is provided within the room of the motor vehicle, the scent holder containing scents bearing materials for emitting different scents useful for a driver of the motor vehicle. Reference data for respective driving conditions of the motor vehicle are stored, the reference data indicating need for supply of respective scents. After storing the reference data, a driving condition of the motor vehicle is detected for producing an electric drive signal representing the driving condition. The drive signal thus produced is compared with a corresponding reference datum for determining whether or not the detected driving condition requires one of the scents contained in the scent holder. When the detected driving condition requires the one scent, one scent bearing material containing the one scent is selected. Then, the one scent from the one scent bearing material is supplied to the room of the motor vehicle.

6 Claims, 3 Drawing Sheets

U.S. PATENT DOCUMENTS

| | | |
|---|---|---|
| 0004039 | 3/1979 | European Pat. Off. . |
| 0123746 | 8/1983 | European Pat. Off. . |
| 0144992 | 12/1984 | European Pat. Off. . |
| 0295129 | 12/1988 | European Pat. Off. . |
| 0345149 | 5/1989 | European Pat. Off. . |
| 2832416 | 2/1980 | Fed. Rep. of Germany . |
| 3446815 | 7/1986 | Fed. Rep. of Germany ...... 340/426 |
| 2573283 | 11/1984 | France . |
| 2596554 | 10/1987 | France ................................. 340/426 |
| 62-49138 | 8/1985 | Japan . |
| 63-160660 | 12/1986 | Japan . |
| 63-308161 | 10/1987 | Japan . |
| 1-123932 | 11/1987 | Japan . |
| 1-186423 | 7/1989 | Japan . |
| 1-302047 | 12/1989 | Japan . |
| 237992 | 8/1925 | United Kingdom . |
| 1172499 | 12/1969 | United Kingdom . |

METHOD OF SUPPLYING SCENTS TO A ROOM OF A MOTOR VEHICLE

BACKGROUND OF THE INVENTION

The present invention relates to a method of supplying scents to a room of a motor vehicle, the scents being selected to meet needs according to information about the drive condition of the motor vehicle.

Conventionally, an aromatic material containing reservoir is placed in a room of a motor-car for repressing odors such as of smoke of cigarette but aromatic materials were not used for exercising their physiological effects on activities of persons in buildings. In U.S. patent application Ser. No. 204,373 filed on June 9, 1988 which is now abandoned and entitled "Method for supplying aromas, apparatus therefor and facilities provided with same", the inventors have proposed as joint inventors a method for supplying aromas to a space, in which aromatic materials are retained in respective reservoirs. At least one of the aromatic materials is selected and volatilized to disseminate aromas thereof according to a timetable which is predetermined on the basis of activities of persons in the space. No attempt has been made to use scents for reducing traffic accidents by exercising excellent physiological effects thereof on drivers of motor vehicles.

Accordingly, it is an object of the present invention to provide a method of supplying scents to a room of a motor vehicle. The method is useful in reducing traffic accidents.

SUMMARY OF THE INVENTION

With this and other objects in view, the present invention provides a method of supplying scents to a room of a motor vehicle. In this method, a scent holder is provided within the room of the motor vehicle, the scent holder containing scents bearing materials for emitting different scents useful for a driver of the motor vehicle. Reference data for respective driving conditions of the motor vehicle are stored, the reference data indicating need for supply of respective scents. After storing the reference data, a driving condition of the motor vehicle is detected for producing an electric drive signal representing the driving condition. The drive signal thus produced is compared with a corresponding reference datum for determining whether or not the detected driving condition requires one of the scents contained in the scent holder. When the detected driving condition requires the one scent, one scent bearing material containing the one scent is selected. Then, the one scent from the one scent bearing material is supplied to the room of the motor vehicle.

DETAILED DESCRIPTION OF THE PREFERRED EMBODIMENTS

Figure 1:
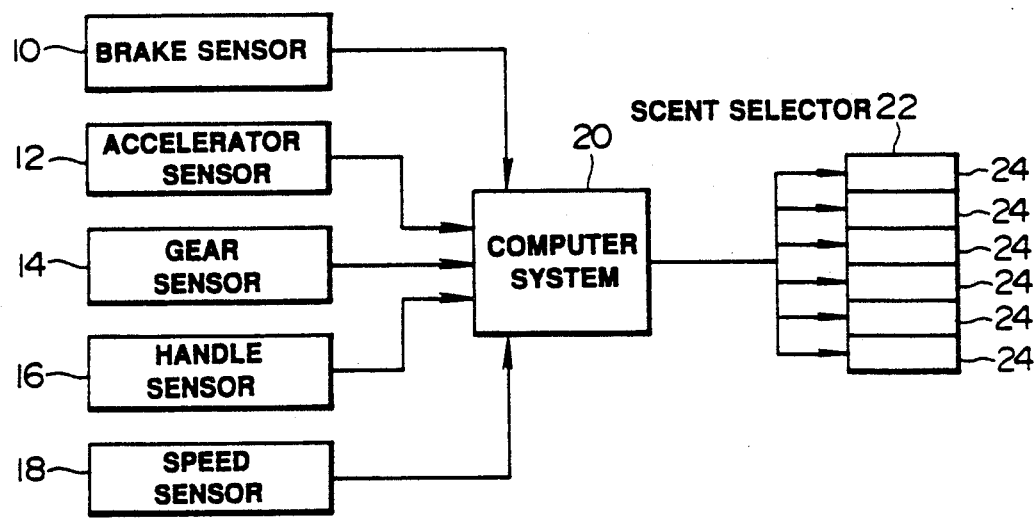
FIG. 1 is a block diagram of a scents supplying apparatus for practising the present invention.
Figure 2:
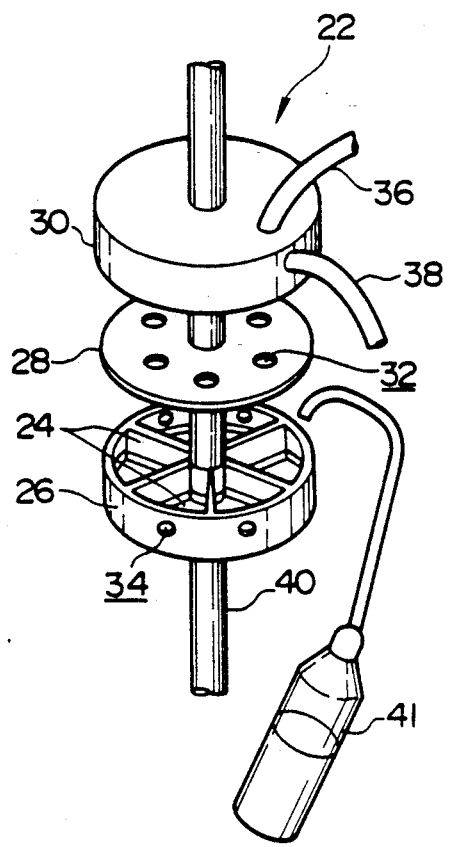
FIG. 2 is a perspective view of the essential part of the scent selector in FIG. 1, parts of the scent selector being axially shifted in position for illustration purpose.

Referring to FIGS. 1 and 2, the scents supplying apparatus according to the present invention is installed in a motorcar. In this embodiment, the scents supplying apparatus includes conventional five sensors: a brake sensor 10 for detecting a torque of a brake pedal; an accelerator sensor 12 for detecting acceleration of the car; a gear sensor 14 for detecting the position of the gear; a steering wheel sensor or handle sensor 16 to detect a rotation angle of the steering wheel; speed sensor 18 for detecting revolution of the wheels. Electric signals from these sensors are transmitted to a controller or a microcomputer system 20 in which the driving conditions of the motorcar is determined, and from which if necessary, a control signal is sent to a scents selector 22 for selecting and discharging a predetermined scent to the room of the motorcar.

The U.S. patent application Ser. No. 204,373 discloses more specific structure of the scent supplying apparatus and the scent selector and the disclosure thereof is incorporated herein by reference. The scents selector 22 has a hollow cylindrical scent receptacle 26 with a bottom wall, the receptacle being coaxially mounted on a rotation shaft 40, which is rotatably mounted to a casing not shown. The scent receptacle 40 has six scent bearing material receiving chambers 24 radially partitioned, of which upper opening ends are sealingly closed with a closure disc 28 slidably mounted around the shaft 40 to form a scent holder. The scent holder is covered with a hollow cylindrical cover 30 rotatably and axially movably mounted around the shaft 40. The cover 30 is stationarily supported on the casing. The scent receptacle 26 has air outlet openings 34 formed through the circumferential wall to correspond to scent bearing material receiving chambers 24. The closure disc 28 have air inlet openings 32 formed through it also to correspond to scent bearing material receiving chambers 24. The cover 30 has an air intake conduit 36 mounted to the top plate thereof and air discharge conduit 38 to the circumferential wall thereof for communicating both the air intake conduit 36 and the air discharge conduit 38 to the inside of the cover 30. The air intake and discharge conduits 36 and 38 are detachably mounted to the cover 30. The rotation shaft 40 is rotated by means of a drive unit 52 (see FIG. 3) for slidably rotating the receptacle 26 to the cover 30 and thereby the air inlet opening and air outlet opening of a specific scent bearing material receiving chamber 24 are communicated to the air supply conduit 36 and the air discharge conduit 38, respectively.

The scent supply apparatus may be incorporated into an air conditioner of the motorcar. Air, introduced from the outside of the car, is preferably added with a specific scent by the apparatus and is then discharged to the room of the car. When air in the car is used, it is deodorized with activated carbon or the like material and is then introduced into the apparatus.

Figure 3:
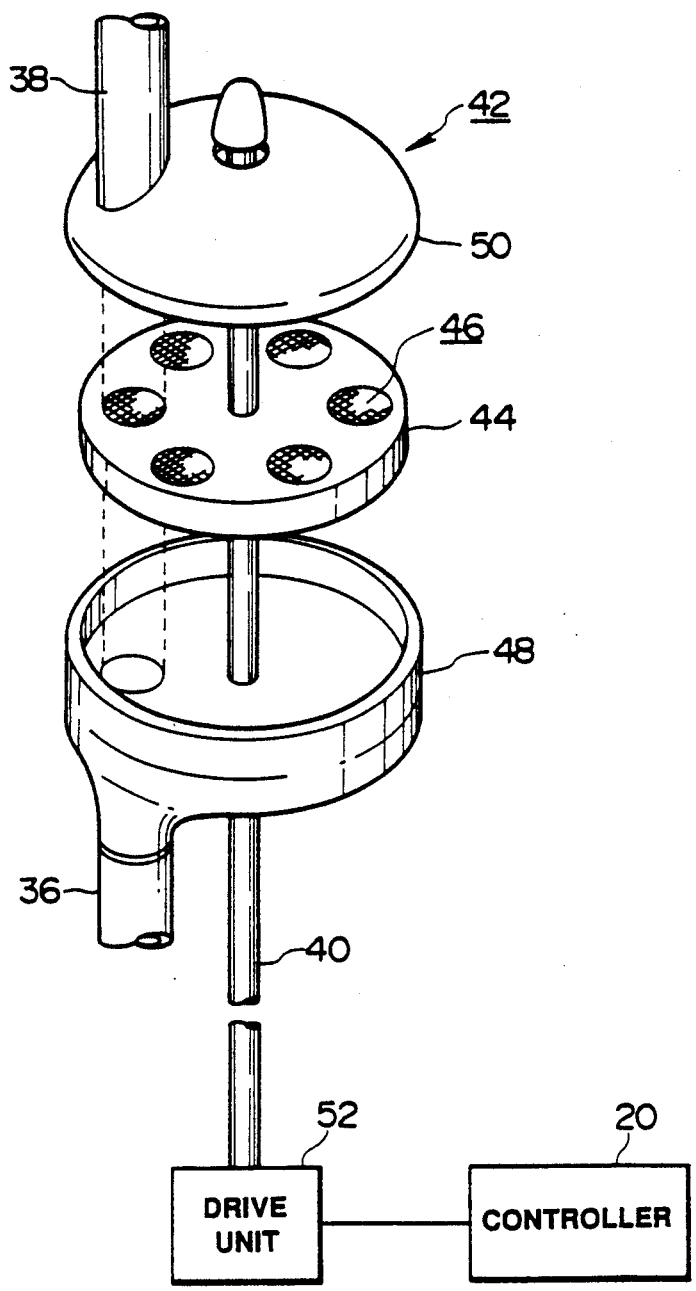
FIG. 3 is a perspective view of a modified form of the scent selector in FIG. 2, parts of the scent selector being also axially shifted.
Figure 4:
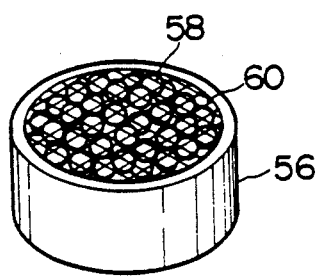
FIG. 4 is an enlarged view of the scent holder used in the scent selector in FIG. 3.
Figure 5:
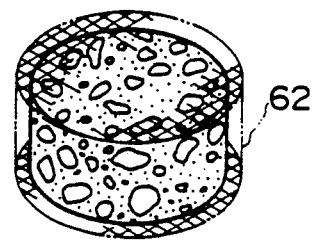
FIG. 5 is an enlarged view of a modified form of the scent holder of FIG. 4.
Figure 6:
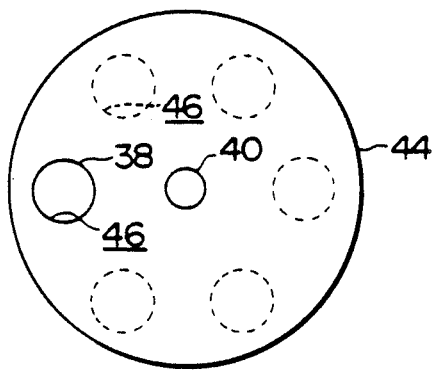
FIG. 6 is an illustration as to how the scent selector is used.
Figure 7:
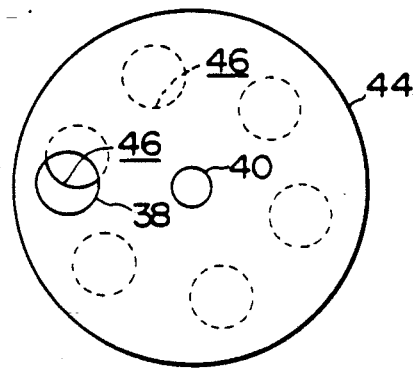

An alternative scent selector 42 is illustrated in FIG. 3. The selector 42 has a scent holding disc 44 coaxially mounted on a rotation shaft 40. The scent holding disc 44 has six scent bearing materials receiving openings 46 formed through it at equal angular intervals about its axis. One end of the rotation shaft 40 passes through a generally hollow cylindrical casing 48, in which the scent holding disc 44 is received. The other end of the rotation shaft 40 is rotatably supported on a cover disc 50, which is placed over the casing 48 for sealingly receiving the scent holding disc 44. The air intake conduit 36 and the air discharge conduit 38 are respectively mounted to the casing 48 and the cover disc 50 so as to communicate to the inside of the casing 48. Each of the scent bearing material receiving openings 46 has a scent cartridge 56 fitted therein, each of which is in the shape of a hollow cylinder as illustrated in FIG. 4. Each scent cartridge 56 has opposite ends closed with net closures 58 and is charged with conventional scent bearing beads 60. Instead of the scent bearing beads 60, use may be made of a sponge 62 containing a liquid fragrance. A specific scent receiving material opening 46 may be fully communicated to the inside of the motor vehicle by bringing it to exactly correspond to the air discharge conduit 38 (air supply conduit 36) as in FIG. 6. The opening 46 may be half communicated to the room of the car by corresponding it to the air discharge conduit 38 as shown in FIG. 7. According to this manner, the supply of the scent may be varied.

Before operating the scents supply apparatus, various scent bearing materials are charged into respective scents bearing materials receiving chambers 24 (or openings 46) by means of a scent supplier 41, and reference data of driving conditions of a motorcar which require supply of respective scents are input into and stored in the microcomputer system 20. In operation, the sensors 10, 12, 14, 16 and 18 send electronic drive signals, representing driving conditions of the motor vehicle, to the computer 20, where the drive signals are compared to respective reference data stored in it. When the brake sensor 10 sends a drive signal, which indicates the motor vehicle is in a hard braking state, to the computer 20, it recognizes such a state by the comparison of the drive signal with the corresponding reference data and thereby send a control signal to the drive unit 52 for angularly moving the receptacle 26 (or disc 44) a predetermined angle to communicate the air inlet opening 32 and air outlet opening 34 of a scent bearing material receiving chamber 24 (or opening 46) to the air intake conduit 36 and air discharge conduit 38, respectively. The scent bearing material receiving chamber 24 has a material, bearing a scent having a stimulant effect, filled in it just below the air outlet opening 34. Thus, air is introduced from the air intake conduit 36 through the air inlet opening 32 into the chamber 24, where the air is aromatized with the scent by volatilizing the scent material. The aromatized air is discharged through the air discharge conduit 38 to the room of the motorcar by making the pressure of the outlet end of the air discharge conduit 38 a negative pressure with a fan not shown. The scent bearing material may contain an aroma of lemon. The hard braking state may be such that the motorcar is decelerated twice or more within 20 seconds.

When the motor vehicle is caught in a traffic jam, the speed sensor 18 detects the revolution of the wheels to send a drive signal, indicating that the car is in a very slow state, to the computer 20, where the signal is compared with the corresponding reference data to thereby determine the drive signal is equal or smaller than the reference data. Thus, the computer 20 angularly moves the scent receptacle 26 or disc 44 at a predetermined angle to communicate a chamber 24 or opening 46, which contains a scent bearing material, to the room of the motor vehicle in the same manner as in the hard braking state. The scent bearing material contains a scent, such as an aroma of lavender, which has an effect in reducing stress due to the traffic jam. The very low state of the car may be such that it travels about 5 km/hour or slower for about 1 minute or more. In such a state, it preferable to supply the scent to the room of the motor vehicle intermittently, for example, every 30 seconds. The very low speed may be conventionally recognized by detecting low gear transmission or by sensing idling of the engine, that is, the state at about 1000 rpm or smaller.

The rapid steering of the motor vehicle may be determined both by sensing with the conventional engine sensor a high revolution of the engine, for example, about 3000 rpm or more, and by detecting a large rotational or steering angle of the steering wheel with a steering wheel sensor or handle sensor 16. In such a case, an aroma of lemon may be supplied to the room of the motor vehicle in the same manner as in the hard braking. The rapid acceleration of the car may be similarly detected by monitoring the opening of an air suction valve of the carburetor. Also in this case, an aroma of lemon may be supplied.

According to the scents supply apparatus, the following further effects may be achieved: in a monotonous steering of the motor vehicle, such as in an expressway, an aroma having a stimulating effect may be supplied at predetermined time intervals to provide the driver with appropriate stimulation; leakage or running out of gasoline may be detected by supplying a strong smell to the driver; and the opening and closing of the doors of the car may be notified to the driver by providing a scent to the room of the car.

Scents may be supplied according to the physiological state of the driver. For a driver with depressed physiological functions in the morning, a scent which activates his circulatory functions may be provided at a predetermined time with a timer which actuates the computer system 20.

It is preferable to adjust the concentration of scents according to purposes. For reducing stress, for example, in a traffic snarl, a scent may be supplied at just above the threshold value which can be detected by nose of a driver. The value may be 1 $\mu$g/liter although it depends on the kind of the scent. In hard braking, a high concentration of a scent, say 100 $\mu$g/liter or more, is provided to the driver so that he or she is able to detect the scent as soon as possible.

We claim:

1. A method of supplying scents to a room of a motor vehicle comprising the steps of:
   providing a scent holder within the room of the motor vehicle, the scent holder including means for containing scent bearing materials and means for selectively emitting a scent from a respective said scent bearing material for a driver of the motor vehicle;
   providing sensor means for sensing at least one driving condition of the motor vehicle and producing a signal representative of each said driving condition;
   providing control means operatively coupled to said sensor means and operatively coupled to said scent holder, said control means including means for storing reference data, means for comparing signals from said sensor means with said reference data, and means for selectively actuating said scent holder to release a said scent;

storing reference data for driving conditions sensed by said sensor means, said reference data identifying conditions for supplying a said scent to the room of the motor vehicle;

after storing reference data, sensing at least one driving condition of the motor vehicle and producing a signal representative of each said driving condition;

comparing each said signal with corresponding reference data; and when said sensed driving condition corresponds to said reference data, controlling said scent holder so as to supply a said scent from one of said scent bearing materials to the room of the motor vehicle.

2. A method as in claim 1, wherein said step of supplying a scent comprises supplying air to one of said scent bearing materials and discharging said scent from said scent holder to the room of the motor vehicle.

3. A method as in claim 2, wherein said scent holder comprises a plurality of partitioned chambers, each for sealingly receiving a respective scent bearing material and wherein said step of controlling said scent holder comprises communicating one of said partitioned chambers with the room of the motor vehicle, volatizing the scent contained in said respective scent bearing material and discharging air containing the volatized scent into the room.

4. A method as recited in claim 3, wherein said step of providing a scent holder comprises mounting an air supply conduit and an air discharging conduit to a casing covering a scent holder, said air discharging conduit being in communication with the room of the motor vehicle and wherein said step of selecting one of said partition chambers comprises angularly rotating the scent holder about an axis thereof so as to communicate a said partition chamber to both said air supply conduit and said air discharge conduit.

5. A method as recited in claim 4, wherein said step of providing sensor means comprises providing sensor means for sensing hard braking, idling of an engine of the motor vehicle, rapid steering, and rapid acceleration, and wherein said step of storing reference data comprises storing the conditions for hard braking, idling of an engine of the motor vehicle, rapid steering, and rapid acceleration.

6. A method as recited in claim 5, wherein said scent containing materials comprise a material having a lemon scent and material having a lavender scent and wherein said control means actuates the scent holder to generate the aroma of lemon when the reference data conditions of rapid steering, hard braking and rapid acceleration are detected and actuates the scent holder to generate the aroma of lavender when the reference data condition of idling of the engine is detected.

* * * * *